United States Patent [19]

Moulton

[11] Patent Number: 5,104,809
[45] Date of Patent: Apr. 14, 1992

[54] METHOD OF MEASURING HYDROQUINONE LEVELS IN BOILER FEEDWATERS USING ELECTROCHEMISTRY

[75] Inventor: Roger D. Moulton, The Woodlands, Tex.

[73] Assignee: Betz Laboratories, Inc., Trevose, Pa.

[21] Appl. No.: 651,159

[22] Filed: Feb. 6, 1991

[51] Int. Cl.$^5$ .................. G01N 33/00; C23F 11/06; L23F 11/04
[52] U.S. Cl. ........................ 436/96; 422/13; 422/16; 422/53
[58] Field of Search ............ 436/96; 422/53, 13, 422/16

[56] References Cited

U.S. PATENT DOCUMENTS 4,541,932  9/1985  Muccitelli .................. 210/750

OTHER PUBLICATIONS

*Journal of High Resolution Chromatography and Chromatograph Communications,* Masoud & Dubes, vol. 3, issue 3, 1980, pp. 132–142.

*Arab Gulf Journal of Sci. Res., A,* Al-Tamrah, vol. 6(3), 1988, pp. 363–375.

Primary Examiner—John W. Rollins
Attorney, Agent, or Firm—Alexander D. Ricci; Philip H. Von Neida

[57] ABSTRACT

An improved method of electroanalytical detection of residual hydroquinone in boiler feedwater employing adding an ionic base and a copper chelant to the feedwater sample. $Na_3PO_4$ and ethylenediamine are representative chemicals when square wave voltammetry (SWV) is used as the electroanalytical technique.

7 Claims, No Drawings

METHOD OF MEASURING HYDROQUINONE LEVELS IN BOILER FEEDWATERS USING ELECTROCHEMISTRY

FIELD OF THE INVENTION

This invention relates to an improved method of measuring by electroanalytical technique residual hydroquinone in boiler feedwaters. More particularly, this invention relates to the addition of an ionic base and a copper Cu(II) chelant to boiler feedwaters to determine residual hydroquinone levels by electroanalytical techniques.

BACKGROUND OF THE INVENTION

The efficient operation of boilers and other steam generating equipment requires chemical treatment of feedwaters to control corrosion. Oftentimes this corrosion is a result of oxygen attack of the metal components in contact with the water in the steam generating equipment.

Oxygen attack is unavoidably accelerated by the high temperatures often found in steam generating systems.

The corrosion is in the form of pitting which is a highly concentrated corrosion affecting only a small area relative to total metal surfaces of the system. This, however, can be a serious problem causing metal failure even though the metal loss is small and the overall corrosion rate is low.

The severity of oxygen attack is dependent on the concentration of dissolved oxygen in the water, the water pH and the temperature of the system. As water temperatures increase, enough driving force is added to the corrosion reaction that even small amounts of oxygen dissolved in the water can cause serious problems. Oxygen pitting is a serious problem in steam generating systems, even where only trace amounts of oxygen are present.

Deaeration is a widely used method for removing oxygen from an aqueous medium. The deaeration of boiler feedwater can be either mechanical or chemical.

While vacuum deaeration has proven to be a useful mechanical deaeration method for treating water distributing systems, boiler feedwater is treated using pressure deaeration with steam as the purge gas. According to the pressure deaeration method for preparing boiler feedwater, the water is sprayed into a steam atmosphere and is heated to a temperature at which the solubility of oxygen in the water is low. About 90 to 95 percent of the oxygen in the feedwater is released to the steam and is purged from the system by venting.

Mechanical deaeration is considered an important first step in removing dissolved oxygen from boiler feedwater. However, as already noted, as water temperature increases, even trace amounts of dissolved oxygen can cause serious problems. Accordingly, supplemental chemical deaeration is often required.

Hydroquinone is often used as an oxygen scavenger for the chemical deaeration of feedwater. However residual levels of hydroquinone will decompose and cause further acid-induced corrosion.

Therefore, it is often necessary to test boiler waters for residual levels of hydroquinone so that appropriate chemical treatment can be applied to neutralize the corrosive effects of hydroquinone decomposition.

SUMMARY OF THE INVENTION

This invention relates to a method of measuring using an electroanalytical technique the level of residual hydroquinone in boiler feedwaters comprising adding to said feedwaters an effective amount for the purpose of an ionic base and a copper chelant.

Accordingly it is an object of the present invention to measure the level of residual hydroquinone in boiler feedwater by adding to a sample of the feedwater an ionic base and a copper chelant and measuring the level of residual hydroquinone by an electroanalytical technique.

These and other objectives and advantages of the present invention will be apparent to those skilled in the art upon reference to the following description of the preferred embodiments

DESCRIPTION OF THE RELATED ART

U.S. Pat. No. 4,541,932 (Muccitelli) discloses a composition and methods of using hydroquinone as a catalyst for oxygen scavengers in boiler systems.

*Journal of High Resolution Chromatography and Chromatograph Communications.* A.N. Masoud and G.R. Dubes, Vol, 3, issue 3, 1980, pages 133-142, disclose a method of detecting hydroquinone as an impurity in reagent grade phenol. This method employs high-performance liquid chromatography with ultra-violet and electrochemical detectors.

*Arab Gulf Journal of Sci. Res..* A. S.A. Al-Tamrah, Vol. 6 (3), 1988, pages 363-375, discloses a method of measuring the levels of concentration of a mixture of p-benzoquinone and hydro quinone. The method is based on the reaction of piperazine with p-benzoquinone at pH of 5.4. The colorimetric determination is measured at 363 nm.

DETAILED DESCRIPTION OF THE INVENTION

This invention relates to a method of measuring the amount of residual hydroquinone in boiler feedwaters of the type containing copper employing an electroanalytical technique, the improvement comprising adding to said boiler feedwaters an effective amount for the purpose of an ionic base which maintains the pH of said boiler feedwaters in a range of 9 to 11 and increases the ionic conductivity of said boiler feedwaters and a copper chelant which complexes with the copper present in said boiler feedwaters and thereby employing an electroanalytical technique to measure the concentration of residual hydroquinone.

Hydroquinone is commonly added to boiler feedwater systems as an oxygen scavenger or as a catalyst for other oxygen scavengers.

It is desirable to measure any residual levels of hydroquinone as its decomposition products can cause acid-induced corrosion of the metal structural surfaces in the boiler. Measuring these hydroquinone levels in conjunction with residual oxygen levels allows both oxygen-induced and acid-induced corrosion reactions to be minimized.

The present inventor has discovered a method of hydroquinone detection that is more sensitive and selective than other analytical methods. This method eliminates impurity interferences by employing an electroanalytic method on a boiler feedwater sample to which an ionic base and a copper chelant has been added.

Older reagent tests involve a chemical reaction between the residual oxygen scavenger and the reagent. When the reaction is complete, the concentration of the reduced reagent is measured. For example, ferric or oxidized leucocrystal violet is added to the sample, which reacts with the oxygen scavenger, and produces ferrous or leucocrystal violet. The concentration of the reduced reagent is measured from the amount of light the solution adsorbs in a spectrometer. Hydroquinone levels can be measured to an accuracy of 100 ppb with this technique. Electrochemical methods such as that employed in the instant invention provide better sensitivity. In addition, all scavengers such as hydrazine, hydroquinone, sulfite and ascorbic acid will respond to the reagent test whereas electrochemical methods are specific and selective to hydroquinone residual only.

Ionic bases that are useful in this invention include $Na_3PO_4$. The present inventor anticipates that the borate, carbonate and hydroxide ionic salts of sodium, potassium and ammonium will also be useful in the present invention.

Representative copper chelants include phenanthroline, asparagine, histidine, pyrazole, ethylenediamine and aminohydroxypyridine.

The ionic base can be added from 1mM to 1M concentration. The chelant is added in excess of demand at a ratio of up to 100 to 1.

The detector used in this invention should be sensitive to hydroquinone concentration of 10 to 100 ppb, even in the presence of residual oxygen, Cu(II), Fe(II), amines and other oxygen scavengers or reducing agents. A Princeton Applied Research Potentiostat Model 273 was used in the inventor's experiments. It is anticipated that any other commercial or home built potentiostat with the same capabilities would perform similarly in this invention.

The potentiostat used employed the square wave voltammetry (SWV) electrochemical technique. However, this invention can use a variety of electrochemical techniques to detect hydroquinone. Cyclic voltammetry, chronoamperometry and chronopotentiometry were all tested. The inventor anticipates that differential pulse polarography may also be an appropriate electrochemical detection technique. The choice of electrode and preparation of the test solution will necessarily be similar regardless of the electrochemical technique to achieve the desired sensitivity.

Square wave voltammetry (SWV) was the electrochemical technique used to test the invention because of its greater selectivity and sensitivity for hydroquinone. This technique is most sensitive when the analyte is Nernstian. For hydroquinone, this is only in the pH range of 9 to 11. That is one function of the ionic base, to maintain the feedwater sample pH in this range. Another function is to increase the ionic conductivity of the feedwater as feedwaters typical of boiler systems are high purity with few ions and cannot support the electrical current the test method requires.

SQUARE WAVE VOLTAMMETRY MEASUREMENT

The detection limit of hydroquinone ($C_o$) can be determined from the Faradaic current (i) reaction:

$$i = nF A C_o m_o$$

where
n = number of electrons removed per molecule during the oxidation reaction
n = 2 for hydroquinone at pH of 9-11
F = Faraday constant = 96484.6 c/eq.
A = Electrode area
$m_o$ = mass transfer coefficient The choice of electrochemical technique determines the value of $m_o$. By keeping the pH of the feedwater test sample in the range of 9-11 the oxidation reaction is kept Nernstian. The reaction products of oxygen with hydroquinone do not interfere with the electrochemical reaction or the measurement of the hydroquinone levels.

EXPERIMENTAL

The purpose of the experiment was to determine which boiler feedwater contaminants gave a square wave voltammetric response at −0.1V vs SCE (saturated calomel electrode). This value was chosen because the hydroquinone concentration is determined from its SWV response measured at its largest value, −0.1 V at pH 10. Those contaminants that gave a response at −0.1 V would interfere with the hydroquinone concentration measurement.

Square wave voltammetry was performed on a boiler feedwater sample taken from a research boiler. The frequency was kept at 1 Hertz to allow the non-Faradaic contribution to the current to decay. 1 mM $Na_3PO_4$ was added to the sample to increase its conductivity and to keep the pH above 9.

A glassy carbon electrode was used as it was found to give the lowest background currents under the experimental conditions.

0 to 68 ppb of hydroquinone was added to the sample. A linear relationship between the hydroquinone concentration and the size of the oxidation peak is clearly evident at −0.1V vs. SCE. The inventor estimates that the detection limits of hydroquinone in these circumstances to be in the range of 5 to 10 ppb.

The possible interfering impurities were then added:

| Species | Amount |
|---|---|
| Cu(II) | 100 ppb |
| Fe(II) | 300 ppb |
| Hydrazine | 1.05 ppm |
| Ascorbic Acid | 1 ppm |
| Morpholine | 300 ppb |
| Oxygen | 8 ppm |

Their redox potentials are shown in Table I

TABLE I

| Species | SWV Peak Potential (vs. SCE) |
|---|---|
| Cu(II) | −0.09 V |
| Fe(II) | none observed |
| Hydrazine | +0.40 V |
| Ascorbic Acid | +0.20 V |
| Morpholine | none observed |
| Oxygen | −0.30 V |

DISCUSSION

Only Cu(II) and oxygen were near enough to the −0.1 V sampling point for hydroquinone to present any significant interference in measuring hydroquinone concentration. Oxygen's redox value is different enough that it would only present a problem if it was in tenfold excess relative to hydroquinone. This is very unlikely in boiler feedwaters.

Cu(II), expressed as $Cu(H_2O)_6^{+2}$, presents a serious interfering presence. The present inventor has found that a copper chelant complexing agent will change the reduction potential of copper to more negative values and "mask" the interfering effects of Cu(II). Those copper chelants that prove useful in the invention include phenanthroline, asparagine, histidine, pyrazole, ethylene diamine and aminohydroxypyridine. Ethylenediamine is particularly preferred. All these compounds have the ability to change the ligand field of Cu(II) and remove it as an interference.

While this invention has been described with respect to particular embodiments thereof, it is apparent that numerous other forms and modifications of this invention will be obvious to those skilled in the art.

Having thus described the invention, what I claim is:

1. A method of measuring the amount of residual hydroquinone in boiler feedwaters of the type containing copper employing an electroanalytical technique, the improvement comprising adding to said boiler feedwaters an effective amount for the purpose of an ionic base which maintains the pH of said boiler feedwaters in a range of 9 to 11 and increases the ionic conductivity of said boiler feedwaters and a copper chelant which complexes with the copper present in said boiler feedwaters and thereby employing an electroanalytical technique to measure the concentration of residual hydroquinone.

2. A method according to claim 1 wherein said electroanalytical technique is square-wave voltammetry.

3. A method according to claim 1 wherein said ionic base is $Na_3PO_4$.

4. A method according to claim 3 wherein said $Na_3PO_4$ is added to said boiler feedwaters in a range of about 1 mM to about 1M concentration.

5. A method according to claim 1 wherein said copper chelant is ethylenediamine.

6. A method according to claim 5 wherein said copper chelant is added to said boiler feedwaters in excess of demand at a ratio up to 100 to 1.

7. A method according to claim 2 wherein said square wave voltammetry is performed on said boiler feedwaters at $-0.1$ V vs SCE.

* * * * *